United States Patent
Bzdusek (10) Patent No.: US 11,517,766 B2
(45) Date of Patent: Dec. 6, 2022

(54) TUNING MECHANISM FOR OAR AND TARGET OBJECTIVES DURING OPTIMIZATION

(71) Applicant: KONINKLIJKE PHILIPS N.V., Eindhoven (NL)

(72) Inventor: Karl Antonin Bzdusek, Madison, WI (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 210 days.

(21) Appl. No.: 16/632,445

(22) PCT Filed: Jul. 31, 2018

(86) PCT No.: PCT/EP2018/070777
§ 371 (c)(1),
(2) Date: Jan. 20, 2020

(87) PCT Pub. No.: WO2019/025460
PCT Pub. Date: Feb. 7, 2019

(65) Prior Publication Data
US 2020/0206534 A1    Jul. 2, 2020

Related U.S. Application Data

(60) Provisional application No. 62/638,388, filed on Mar. 5, 2018, provisional application No. 62/538,856, filed on Jul. 31, 2017.

(51) Int. Cl.
*A61N 5/10* (2006.01)
(52) U.S. Cl.
CPC ......... *A61N 5/1031* (2013.01); *A61N 5/1039* (2013.01); *A61N 5/1045* (2013.01)

(58) Field of Classification Search
CPC .... A61N 5/103; A61N 5/1031; A61N 5/1038; A61N 5/1039; A61N 5/1045; A61N 2005/1034
See application file for complete search history.

(56) References Cited

U.S. PATENT DOCUMENTS

2004/0165696 A1 *   8/2004  Lee .................. G16H 30/20
                                              378/65
2010/0046706 A1 *   2/2010  Moreau ............. A61N 5/1047
                                              378/65

(Continued)

FOREIGN PATENT DOCUMENTS

CN      105447330 A     3/2016
CN      105930637 A     9/2016

(Continued)

OTHER PUBLICATIONS

International Search Report and Written Opinion for PCT/EP2018/070777, dated Nov. 26, 2018.

(Continued)

*Primary Examiner* — John P Lacyk (57) ABSTRACT

In radiation treatment planning, a plurality of optimization loops are performed. In each optimization loop computes a dose distribution (60) in a patient represented by a planning image (42) with regions of interest (ROIs) defined in the planning image. Weights (64) for objective functions (50) are determined from objective function value (OFV) (52) for the objective functions. An optimized dose distribution is produced by adjusting the plan parameters to optimize the computed dose distribution respective to composite objective function (62). At least one optimization loop may include updating (70) at least one OFV goal to be used in at least the next performed optimization loop. At least one optimization loop may include updating an objective function quantifying compliance with a target dose for a target (Continued)

ROI based on a comparison of a metric of coverage of the target ROI and a desired coverage of the target ROI.

19 Claims, 6 Drawing Sheets

(56) References Cited

U.S. PATENT DOCUMENTS

| | | | |
|---|---|---|---|
| 2011/0202324 A1* | 8/2011 | Currell | A61N 5/1031 703/2 |
| 2016/0023018 A1* | 1/2016 | Zhang | A61B 5/08 600/1 |
| 2016/0059037 A1 | 3/2016 | Bender | |
| 2017/0014642 A1 | 1/2017 | An | |
| 2017/0087383 A1 | 3/2017 | Peltola | |
| 2017/0173365 A1 | 6/2017 | Bzdusek | |
| 2018/0078792 A1* | 3/2018 | Ollila | A61N 5/1031 |
| 2018/0185669 A1* | 7/2018 | Kuusela | A61N 5/103 |
| 2018/0369611 A1* | 12/2018 | Owens | A61N 5/1039 |
| 2019/0030367 A1* | 1/2019 | Kuusela | A61N 5/1031 |

FOREIGN PATENT DOCUMENTS

| | | |
|---|---|---|
| EP | 3108932 A1 | 12/2016 |
| WO | 2014068435 A2 | 5/2014 |
| WO | 2016198979 A1 | 12/2016 |
| WO | 2017118725 A1 | 7/2017 |

OTHER PUBLICATIONS

Zarepisheh, Masoud et al "Multi-Criteria Framework with Voxel-Dependent Parameters for Radiotherapy Treatment Plan Optimization", Medical Physics, vol. 41, No. 4, Apr. 2014.

Rosen Isaac, et al. "Interactively exploring optimized treatment plans", Int J Radiat Oncol Biol Phys 2005; 61: 570-82.

Gopal, R. et al Plan space: Representation of treatment plans in multidimensional space. Int J Radiat Oncol Biol Phys 2002; 53: 1328-36.

Zhang X, et al. "A sensitivity-guided algorithm for automated determination of IMRT objective function parameters" Med Phys 2006; 33: 2935-44.

Zhang X, et al, A methodology for automatic intensity-modulated radiation treatment planning for lung cancer. Phys. Med. Biol. 2011; 56: 3873-3893.

Zhang, H.H. et al "Modeling plan-related clinical complications using machine learning tools in a Multiplan IMRT framework", Int J Radiat Oncol Biol Phys 2009; 74: 1617-26.

Wu, Binbin et al, "Data-driven approach to generating achievable dose-volume histogram objectives in intensity modulated radiation therapy treatment planning", Int J Radiat Oncol Biol Phys 2011; 79: 1241-7.

Craft, David et al "Improved planning time and plan quality through multicriteria optimization for intensity-modulated radiotherapy", Int J Radiat Oncol Biol Phys 2011.

Wu, Binbin et al "Patient geometry-driven information retrieval for IMRT treatment plan quality control", Med Phys 2009; 36: 5497-505.

Petit, Steven F. et al, "Increased organ sparing using shape-based treatment plan optimization for intensity modulated radiation therapy of pancreatic adenocarcinoma", Radiother Oncol 2011; Article in press, online version.

Wu, Binbin et al, "Using overlap volume histogram and intensity modulated radiation therapy plan data to guide and automate volumetric modulated arc therapy treatment planning: a head-and-neck case study", Int J Radiat Oncol Biol Phys 2012.

Moore, Kevin L. et al "Quantitative Metrics for Assessing Plan Quality", Seminars in Radiation Oncology, vol. 22, Issue 1, Jan. 2020.

* cited by examiner

TUNING MECHANISM FOR OAR AND TARGET OBJECTIVES DURING OPTIMIZATION

CROSS-REFERENCE TO PRIOR APPLICATIONS

This application is the U.S. National Phase application under 35 U.S.C. § 371 of International Application No. PCT/EP2018/070777, filed on Jul. 31, 2018, which claims the benefit of U.S. Provisional Patent Application Ser. No. 62/538,856, filed on Jul. 31, 2017 and U.S. Provisional Patent Application Ser. No. 62/638,388, filed Mar. 5, 2018. These applications are hereby incorporated by reference herein.

FIELD

The following relates generally to the radiation therapy arts, inverse modulated radiation therapy planning arts, modulated arc radiation therapy arts, and the like.

BACKGROUND

Intensity modulated radiation therapy (IMRT) is a known technique for targeted treatment of a malignant tumor. IMRT techniques include conventional IMRT as well as variants such as Intensity Modulated Proton Therapy (IMPT), Volumetric Modulated Arc Therapy (VMAT), Intensity Modulated Arc Therapy (IMAT), and so forth. In radiation treatment planning, a planning image is acquired using transmission computed tomography (CT) or another imaging modality. The dosimetrist contours the target (e.g., a cancerous tumor to be irradiated) and one or more organs at risk (OARs) that are to be spared (at least to some extent) from receiving a large radiation dose. Various objectives are formulated. For a tumor or OAR, some typical objectives include some combination of a minimum dose (Min Dose), a maximum dose (Max Dose), a minimum dose to a given volume (Min dose volume histogram (DVH)), and/or a maximum dose to a given volume (Max DVH). A DVH objective specifies that no more than x % of the ROI volume can exceed the specified minimum (or maximum) dose limit. As an example, a Min DVH objective may specify that no more than 30% of the ROI volume can exceed a certain minimum dose. For the target, a uniform dose objective is another common objective. Additional or other objectives may be employed, for example a maximum equivalent uniform dose objective, or normal tissue complication probability (NTCP) type objectives. In addition to the objective, one or more hard constraints may be imposed on the optimization.

The objectives are formulated into corresponding objective functions. In a conventional formulation, each objective function quantifies the extent of non-compliance with the corresponding objective. Thus, if the corresponding objective is met for all volume elements of the target or OAR to which the objective applies, then the objective function value (OFV) is exactly zero. On the other hand, if the objective is not met for some fraction of volume elements of the target or OAR, then the OFV will be larger than zero, with the magnitude indicating the extent to which the objective is not met. In the illustrative Min DVH with a 30% volume specification, the objective function would quantify non-compliance as the extent to which more than 30% of the volume elements exceed the specified minimum dose. If less than 30% of the total ROI volume exceeds the specified minimum dose then the objective function would return a value of zero (full compliance).

The objective functions are combined to form a composite objective function. Additional inputs include the planning image and contours defining the target and OARs, a radiation delivery device model representing the radiation delivery device which is planned to deliver the radiation treatment, and a parameterized radiation treatment plan whose parameters may be expressed as physically realizable parameters of the radiation source(s) and/or their movement around the patient, or as "virtual" parameters that are subsequently converted to physically realizable parameters. For example, physically realizable parameters for IMRT may include multi-leaf collimator (MLC) settings at control points, as well as speed of beam movement along an arc in the case of IMRT techniques such as VMAT, IMAT, or other radiation treatment techniques in which the radiation beam sources move around the patient, and/or so forth. The "virtual" parameters, if employed, may for example include weights of "beamlets" representing small-area segments of the radiation beam.

With these inputs provided, a dose optimization is performed to adjust the parameters of the radiation treatment plan so as to optimize the delivered radiation dose distribution respective to the composite objective function. The resulting radiation treatment plan is converted to physically realizable parameters (in the case that virtual parameters such as beamlets are used during the dose optimization) and stored in a non-transitory storage medium for later use in executing the radiation treatment.

Radiation treatment planning is a complex process, involving optimization of typically dozens or hundreds of parameters to optimize a composite objective function formed by combining several to several dozen constituent objective functions. In conventional radiation treatment planning, the optimization is done in a manual, ad hoc fashion, and amounts to a "negotiation" between the dosimetrist and the physically realizable dose distributions achievable using the (modeled) radiation delivery device. In a typical workflow, the dose optimization is performed and the OFVs are computed for the optimized dose distribution. The OFVs are presented to the dosimetrist, usually along with other information such as the dose map rendered in three-dimensions (3D) superimposed on the planning image with the target and OAR contours drawn on the rendering, and/or dose volume histogram (DVH) plots for various regions of interest (ROI, e.g. for the target and for various OARs), and/or so forth. Based on this information, the dosimetrist identifies objectives which are not met or which appear to be difficult to meet, and may manually adjust certain objectives (e.g. adjust the maximum or minimum dose specified for a Max Dose or Min Dose objective, and/or adjust the given volume specification in the case of a Max DVH or Min DVH objective) and then re-run the dose optimization. Successive optimization loops of radiation treatment plan optimization followed by presentation of OFVs and other information followed by manual adjustments is repeated perhaps several times or more before arriving at a radiation treatment plan that delivers a dose distribution that is acceptable to the dosimetrist.

More recently, auto-planning approaches have been developed, which automate the manual loops of the radiation treatment planning process. In one approach, a template is employed for the type of radiation treatment to be performed. The template specifies objective functions and corresponding OFV goals. The OFV goals are the OFVs which the dosimetrist typically (e.g. empirically) settles upon after performing the several loops of dose optimization/review of OFVs/manual adjustments. The OFV goals may be specified quantitatively, or using a prioritization scheme, e.g. assigning each objective a priority such as "high", "medium", or "low" priority which are then converted to OFV goals. After the initial dose optimization, the objectives are automatically adjusted based on how well the OFV goals were met, and the dose optimization is then repeated over several automated loops to tune the dose optimization to match the OFV goals. In research studies, auto-planning has demonstrated promise for reducing radiation treatment planning time from hours using conventional manual loops to a few tens of minutes using auto-planning.

The following discloses new and improved systems, device, and methods.

SUMMARY

In one disclosed aspect, a non-transitory storage medium stores instructions readable and executable by a computer to perform a radiation treatment planning method comprising performing a plurality of optimization loops. Each optimization loop includes: computing a dose distribution in a patient represented by a planning image of the patient with regions of interest (ROIs) defined in the planning image wherein the dose distribution is to be delivered by a radiation delivery device (10) represented by a radiation delivery device model executing a parameterized radiation treatment plan; determining weights for objective functions wherein each objective function quantifies compliance of the computed dose distribution with a corresponding objective for a ROI defined in the planning image and the weights are determined from objective function value (OFV) goals for the objective functions; and producing an optimized dose distribution by adjusting parameters of the parameterized radiation treatment plan to optimize the computed dose distribution in the patient respective to a composite objective function comprising a weighted sum of the objective functions weighted by the determined weights for the objective functions. At least one optimization loop further includes updating at least one OFV goal wherein the updated at least one OFV goal is used in at least the next performed optimization loop. An optimized radiation treatment plan is stored in a non-transitory radiation therapy plans storage. The optimized radiation treatment plan comprises the parameterized radiation treatment plan with the adjusted parameters corresponding to the optimized dose distribution produced by the last performed optimization loop of the plurality of optimization loops.

In another disclosed aspect, a radiation treatment planning method is disclosed. Using a computer, a plurality of optimization loops are performed. Each optimization loop includes determining weights for objective functions from at least OFV goals for the objective functions. Each objective function quantifies dose distribution compliance with a corresponding objective for a ROI defined in a planning image of a patient. A dose distribution is computed in the patient represented by the planning image. The dose distribution is to be delivered by a radiation delivery device represented by a radiation delivery device model executing a parameterized radiation treatment plan. An optimized dose distribution is produced by adjusting parameters of the parameterized radiation treatment plan to optimize the computed dose distribution in the patient respective to a composite objective function comprising a weighted sum of the objective functions weighted by the determined weights. At least one optimization loop further includes updating the OFV goal of at least one objective function wherein the updated OFV goal is used in at least the next performed optimization loop.

In another disclosed aspect, a radiation treatment planning apparatus includes an electronic processor and a non-transitory storage medium storing instructions readable and executable by the electronic processor to perform a radiation treatment planning method comprising performing a plurality of optimization loops. Each optimization loop includes computing a dose distribution in a patient represented by a planning image. The dose distribution is to be delivered by a radiation delivery device represented by a radiation delivery device model executing a parameterized radiation treatment plan. An optimized dose distribution is produced by adjusting parameters of the parameterized radiation treatment plan to optimize the computed dose distribution in the patient respective to a composite objective function comprising a weighted sum of objective functions. The composite objective function includes an objective function quantifying compliance with a target dose for a target region of interest (ROI). The target dose is initially set to a prescription dose. At least one optimization loop further includes updating the target dose based on a comparison of a metric of coverage of the target ROI and a desired coverage of the target ROI wherein the updated target dose is used in at least the next-performed optimization loop. In some embodiments, the metric of coverage is a prescription percentage at a specified volume coverage of the target ROI. The updating may comprise increasing the target dose if the prescription percentage determined for the optimized dose distribution is less than the desired prescription percentage at the specified volume coverage of the target ROI. Such an update may include, for example, adjusting the target dose $D_t$ by an amount proportional to $(X\%_{desired} - X\%_{actual})$ where X % actual is the prescription percentage determined for the optimized dose distribution and $X\%_{desired}$ is the desired prescription percentage at the specified volume coverage of the target ROI.

One advantage resides in providing auto-planning of a radiation treatment plan with improved balancing of objectives.

Another advantage resides in providing auto-planning of a radiation treatment plan with improved balancing of objectives for a specific patient.

Another advantage resides in providing auto-planning of a radiation treatment plan with improved robustness against difficult or impossible objective goals.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention. Unless otherwise noted, the drawings are diagrammatic and are not to be construed as being to scale or to illustrate relative dimensions of different components.

DETAILED DESCRIPTION

In existing auto-planning approaches for improving efficiency of radiation treatment planning, OFV goals are defined in a template for the type of radiation treatment being planned. The auto-planning loops then automatically reformulate or adjust the objectives after each optimization loop to more closely match the OFV goals. In this way, successive optimization loops adjust the objectives so as to achieve the balance between the various objectives that would ordinarily be arrived at by tedious manual adjustments of the objectives by a dosimetrist. The auto-planning approach thus automates the negotiation between the various objectives ordinarily performed manually by the dosimetrist.

In existing auto-planning approaches, the OFV goals are fixed template values for the type of radiation treatment being planned. It is recognized herein that this approach may fail to suitably capture patient-to-patient variability. For example, different patients may have different extents of overlap between a tumor and a particular OAR. In such a case, patients with larger overlap of these two ROIs may appropriately have larger OFV goals for the OAR, since the larger overlap may limit the extent to which the OAR sparing can be driven in those patients. By contrast, patients with less overlap, or no overlap, between these two ROIs may appropriately have smaller OFV goals for the OAR which are likely achievable since the small or non-existent overlap provides greater flexibility for the dose optimization to spare the OAR.

More generally, it may occur that as the auto-planning proceeds an OFV goal for an objective may be difficult to reach, or may even be unattainable. In this case, successive optimization loops will continue to strive to meet the OFV goal by repeatedly reformulating that objective and possibly other objectives, without success. This process may operate to sacrifice desired dose to the target, and/or to reduce the sparing of critical OARs, while still failing to achieve the difficult or impossible OFV goal.

By enabling adjustment of one or more OFV goals between optimization loops of the auto-planning, as disclosed herein, the extent to which objectives may need to be reformulated or adjusted away from their ideal values is reduced. Moreover, since the OFV goals employ the same quantification as the OFVs displayed for the objective functions, these values are already familiar to the dosimetrist, so that the dosimetrist can readily apprehend the impact of adjusting an OFV goal on the dose to be delivered to the corresponding ROI.

In some disclosed manual embodiments, the user interface displays the OFVs of the objectives for the currently optimized dose distribution, along with the OFV goals. The user can then input a new OFV goal if desired, for example if the dosimetrist sees that the OFV for a particular objective function remains far from the OFV goal after one or more optimization loops.

In some disclosed automated embodiments, an OFV goal is adjusted based on the OFVs of the objective functions for the optimized dose distribution produced by the latest-executed optimization loop. For example, the automatic updating may comprise scaling the OFV goal by a multiplier that is functionally dependent on the OFV of the corresponding objective function for the optimized dose distribution produced by the optimization loop, e.g. dependent on the ratio of the OFV goal to the current OFV raised to a power that is tuned to provide a desired level of damping for the goal adjustment.

These are merely illustrative examples. The disclosed approach of adjusting the OFV goals has substantial advantages. Basing the OFV goals on target only OFVs, as in some illustrative embodiments, balances the OAR OFVs with the target OVFs thus allowing the user to adjust the ratio. Since the target only OFVs are different for each case, adjusting the OVF goals achieves a consistent balance across patients. In the case where a target only OFV is low, the fixed OFV goals are going to be relatively high compared to the target sacrificing target coverage. In the case where a target only OFV is high, the OAR goals are relatively low and desired sparing may not occur.

Figure 1:
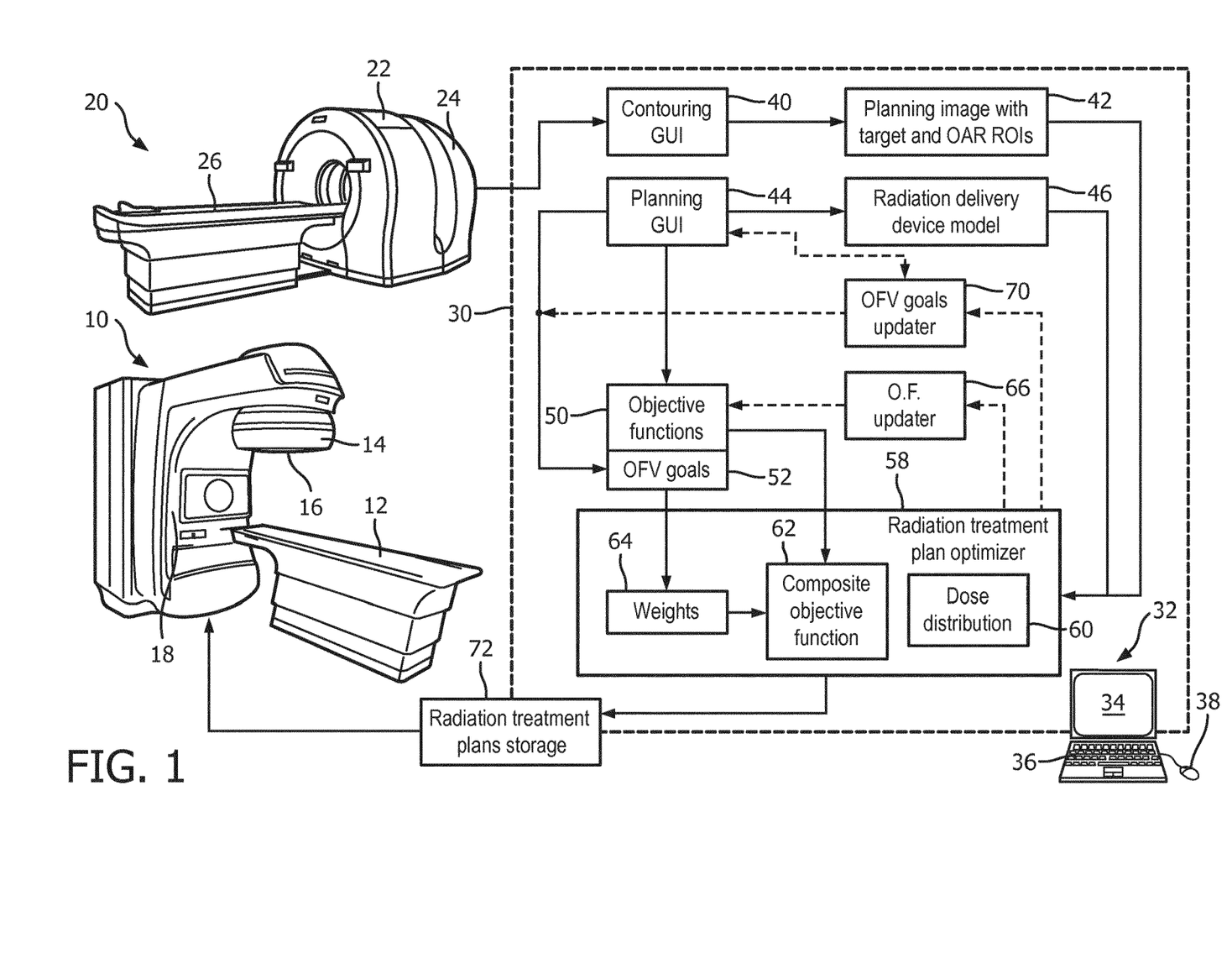
FIG. 1 diagrammatically shows a radiation treatment system.

With reference to FIG. 1, a radiation therapy planning and delivery system is diagrammatically shown. The radiation therapy may be any type of radiation therapy employing therapeutic radiation beams, e.g. electron beams, proton beams, high energy x-ray beams, or so forth. The radiation treatment may employ a discrete "step-and-shoot" approach in which a radiation beam source is stepped between successive fixed positions along a trajectory that partially or entirely encircles the patient. Alternatively, the radiation treatment may employ a continuous arc radiation therapy, such as Volumetric Modulated Arc Therapy (VMAT), Intensity Modulated Arc Therapy (IMAT), or so forth, in which the radiation beam source continuously irradiates the patient as the beam is revolved around the patient along a partially or entirely encircling trajectory. The number of beams may be one, two, three, or more. In the case of continuous arc radiation therapy, the number of arcs executed in the therapy session may, in general, be one, two, three, or more. By way of non-limiting example, an illustrative radiation delivery device 10 is a linear accelerator (linac) with a couch 12 for loading and supporting the patient. In some embodiments, the couch 12 provides three degrees of translational freedom of movement and optionally also three degrees of rotational freedom of movement, with couch position settings optionally being parameters of the parameterized radiation treatment plan to be executed by the radiation delivery device 10. The illustrative linac 10 includes a linear electron beam accelerator (internal component not shown) which energizes an x-ray or gamma ray generator and associated hardware which serves as the radiation source 14. A multi-leaf collimator (MLC) 16 comprises adjustable leaves that can be set to shape the radiation beam during the radiation treatment, and these MLC settings can also be parameters of the parameterized radiation treatment plan. In some embodiments, the MLC 16 can be rotated to a chosen collimator angle, which again may be a plan parameter. The radiation source 14 can be rotated along a trajectory encircling (or partially encircling) the patient by way of rotation of a rotating assembly 18. Various motion settings may be further parameters of the parameterized radiation treatment plan, e.g. a rotation speed. In other radiation delivery device designs, the radiation beam may be stationary and the patient may be rotated or otherwise moved to achieve controlled volumetric radiation delivery. In yet other embodiments, both the patient and the (typically multiple) radiation beams may be fixed, with the use of multiple beams providing controlled volumetric radiation coverage.

Prior to performing a radiation treatment session (which may be a single session, or one session of a plurality of sessions making up a fractionated radiation therapy regimen) using the radiation delivery device 10, a planning image is first acquired of the patient. In the illustrative example, this is done using an illustrative multi-modal imaging device 20 that includes an illustrative computed tomography (CT) imaging gantry 22 and an illustrative positron emission tomography (PET) imaging gantry 24 with a common patient couch 26 for moving the patient into one and/or the other imaging gantries 22, 24. The imaging device 20 may, by way of non-limiting illustration, be an Ingenuity™ time-of-flight (TF) PET/CT scanner, a Gemini™ TF PET/CT scanner, or a TruFlight™ TF PET/CT scanner (each available from Koninklijke Philips N.V., Eindhoven, the Netherlands). It should be noted that a single imaging modality may be used for acquiring the planning image, e.g. only CT. Additional or other imaging modalities may be employed for acquiring the planning images, such as magnetic resonance (MR) images acquired using an MR imaging device, single photon emission computed tomography (SPECT) images acquired using a gamma camera, and/or so forth. The planning images are processed by a radiation therapy planning device 30 comprising a computer 32 (e.g. a desktop computer, network server computer, various combinations thereof, or so forth) that is programmed to provide a user interface and computational processing to generate a radiation therapy plan using planning images acquired by the imaging device 20. For facilitating user interfacing, the computer 32 includes or has access to at least one display 34 (e.g. an LCD display, plasma display, or so forth) and one or more user input devices such as an illustrative keyboard 36, mouse 38, a touch-sensitive overlay of the display 34, and/or so forth. A non-transitory storage medium stores instructions which are readable and executable by the computer 32 to program the computer 32 to implement the radiation therapy planning device 30. The non-transitory storage medium (not shown) may be integral with the computer 32 (e.g. a hard drive of the computer) or accessible by the computer 32 (e.g. a network drive connected to the computer via a hospital data network, the Internet, or some combination thereof). More generally, the non-transitory storage medium may be hard disk or other magnetic storage medium, and optical disk or other optical storage medium, a solid-state drive (SSD) or other electronic storage medium, various combinations thereof, or so forth.

The computer 32 is programmed to provide a contouring graphical user interface (contouring GUI) 40 via which an oncologist, radiologist, or other medical professional can draw 2D and/or 3D contours delineating a target region of interest (ROI) to be irradiated by the radiation therapy and one or more organ at risk (OAR) contours delineating one or more ROIs referred to herein as OARs whose permissible radiation exposure is to be controlled or limited. The contouring GUI 40 can operate in various known ways. For example, the user may manually draw 2D contours around the target or OAR in various 2D planning slices of a 3D planning image using a pointing device such as the mouse 38 or a touch screen, and the computer 32 is programmed to interpolate between these 2D contours to generate a 3D contour (sometimes called a mesh) delineating the planning target volume (PTV) or OAR. In a more automated approach, the user may identify a small number of landmarks that mark boundary points of the PTV or OAR and the computer 32 is programmed to define an initial 3D mesh including these landmarks and then fit the initial mesh to the PTV or OAR using a mesh fitting approach that detects feature edges based on spatial gradients or the like. In a fully automated approach the initial mesh may be automatically generated based on a reference geometry, and the fitted mesh presented to the user for final adjustment (if needed) and approval. These are merely illustrative examples. The output of the contouring includes the planning image with delineated target and OAR ROIs 42.

A planning GUI 44 provides user interfacing via which the dosimetrist selects and guides optimization of a parameterized radiation therapy plan. Via the planning GUI 44 the radiologist selects a radiation delivery device model 46 that represents the radiation delivery device 10 that is to be used to deliver the radiation therapy, in the device configuration that is to be used. Some configuration settings may be parameters of the radiation therapy plan which are to be optimized. The planning GUI 44 also provides user interfacing via which the dosimetrist selects or constructs the initial objective functions 50 and objective function value (OFV) goals 52. In some embodiments, the device model 46, default objective functions 50 and default OFV goals 52 are loaded by loading a template for the particular type of radiation therapy being planned (e.g. specified by the organ being irradiated and a set of standard ROIs). The template is suitably displayed via the planning GUI 44 as a table or spreadsheet with editable fields allowing the dosimetrist to edit parameters of the objective functions (e.g. maximum or minimum dose values, and volume percentages for DVH objectives, maximum equivalent uniform dose objective, normal tissue complication probability (NTCP) type objectives, or so forth) and the OFV goals. Preferably the template allows for entry of additional objective functions (e.g. as new rows of the table or spreadsheet) or deletion of one or more default objective functions.

The planning image with ROIs 42, the radiation delivery device model 46, the objective functions 50, and the OFV goals 52 serve as inputs to a radiation treatment plan optimizer 58 that optimizes a dose distribution 60 with respect to a composite objective function 62 comprising a weighted sum of the objective functions 50 weighted by weights 64 for the objective functions 50 determined from OFV goals 52 for the (corresponding) objective functions. In one approach for computing the weights 64, the dose distribution 60 in the patient (as represented by the planning image with ROIs 42) is initially computed. This initial dose distribution is the dose that is calculated would be delivered by the radiation delivery device 10 represented by the radiation delivery device model 46 executing the initial parameterized radiation treatment plan. The weights 64 for the objective functions 50 are then determined from the OFV goals 52 for the objective functions and the actual OFVs of the objective functions 50 computed for the initial dose distribution. One suitable formulation of the weight 64 for an objective function is to scale a default weight value based on a ratio of the OFV goal for that objective function and the actual OFV for that objective function. This ratio reflects how closely the initial dose distribution comes to the OFV goal. If there is no OFV available, e.g. in the first iteration if the OFVs are not initially computed, then default weights may be used to start the iterative process. For example, each default weight can be set to one of three values corresponding to objectives with low, medium, or high priority, respectively.

With the weights 64 set for the initial optimization loop, the radiation treatment plan optimizer 58 proceeds to produce an optimized dose distribution by adjusting parameters of the parameterized radiation treatment plan to optimize the computed dose distribution 60 in the patient respective to a composite objective function 62 comprising the weighted sum of the objective functions 50 weighted by the determined weights 64 for the objective functions. This optimization can use any suitable optimization algorithm, e.g. a least squares minimization or so forth. For the illustrative objective functions which produce an OFV of zero for full compliance with an objective and an increasing OFV for increasing magnitude of non-compliance with the objective, the optimization suitably minimizes the composite objective function 62. The output of this optimization is a set of OFVs for the objective functions 50, along with the optimized computed dose distribution 60.

As in conventional auto-planning, after the dose optimization, the radiation therapy planning device 30 includes an objective functions updater 66 in which the computer 32 is programmed to automatically adjust (i.e. reformulate) the objective functions 50 based on how well the OFV goals 52 were met. Some approaches for re-formulating the objectives are described, for example, in WO 2014/068435 A2 published May 8, 2014. In some reformulation approaches there described, the current OFVs may be compared to the corresponding OFV goals 52. If the current OFV is less than the OFV goal, the parameters of the objective function (e.g. the minimum or maximum dose, and/or the volume percentage in the case of a DHV goal) are modified to increase the OFV to approximately the OFV goal. Conversely, if the current OFV is greater than the OFV goal, the parameters of the objective function are modified to decrease the OFV to approximately the OFV goal. In addition to modifying the parameters of the objective functions, additional dose objectives can be added by the objective functions updater 66 for high priority structures and/or the weights of existing objectives can be adjusted by scaling the weight by the ratio of the OFV goal versus the current OFV for the objective function. For example, a high weight objective can be added for a high priority structure whose objective functions are poorly met, or hot and/or cold spots can be identified (i.e. defined as new ROIs) and objective functions for these spots can be added to improve conformity of the dose distribution to target structures. As yet another illustrative example, dose spillage outside of target structures can be identified and objectives (and corresponding objective functions) can be added to reduce the identified spillage.

In addition to providing the objective functions updater 66 to automatically provide auto-planning by adjusting (i.e. reformulating) the objective functions 50, the disclosed radiation therapy planning device 30 further includes an OFV goals updater 70 in which the computer 32 is programmed to adjust the OFV goals 52. In a manual approach, the OFV goals updater 70 operates by invoking the planning GUI 44 to display the OFV goals and the OFVs of the objective functions 50 for the optimized dose distribution 60 produced by the initial (or, more generally, the most recent) optimization loop performed by the radiation treatment plan optimizer 58, and to receive, via a user input device 36, 38 operatively connected with the computer 32, updated values for one or more OFV goals, which are then used in at least the next performed optimization loop of the auto-planning.

In an automated approach, the OFV goals updater 70 operates by automatically updating one or more OFV goals based on the OFVs of the objective functions 50 for the optimized dose distribution 60 produced by the initial (or, more generally, the most recent) optimization loop. In one approach, the automatic updating of one or more of the OFV goals 52 may include scaling the OFV goal by a multiplier that is functionally dependent on the OFV of the corresponding objective function for the optimized dose distribution produced by the optimization loop. In some embodiments, there is an interrelation between the operation of the objective function updater 66 and the OFV goal updater 70. For example, in one approach the objective function updater 66 may operate to adjust the minimum (or maximum) dose parameter of the objective function unless that adjustment is determined to be unacceptable, for example because the target(s) are significantly degraded (one indication is a large objective function value). If the adjustment of the dose parameter of the objective function is deemed to be unacceptable then this is an indication that the OFV goal may be too high, and accordingly the OFV goal updater 70 then operates to adjust the OFV goal to a more balanced value.

After adjustment (i.e. reformulation) of objective functions and adjustment of OFV goals, the next loop is performed by again computing the weights 64 (now using the updated OFVs and any updated OFV goals) and updating the composite objective function 62 with the recomputed weights 64 and to include any additional objective function(s) added by the objective functions updater 66 or to reflect removal of any objective function(s) by the objective functions updater 66. The dose distribution 60 is again optimized now using the updated composite objective function 62, followed again by objective function reformulation and OFV goal adjustment, and such loops are repeated one or more times. Also note that the OFV goals can be updated at a different rate than the objective function parameters (weight, dose level, etc). For example, the OFV goals may be updated only every second loop. The final loop outputs the parameterized radiation treatment plan with final auto-planning optimized parameters, which is stored in a radiation treatment plans storage 72 (e.g. on a hard disk drive, or SSD, or other non-transitory storage medium). At the scheduled time, the patient comes to the radiation therapy laboratory and is loaded into the radiation delivery device 10, which retrieves the parameterized radiation treatment plan with final auto-planning optimized parameters and delivers radiation treatment to the patient in accord with the retrieved optimized radiation treatment plan.

Figure 2:
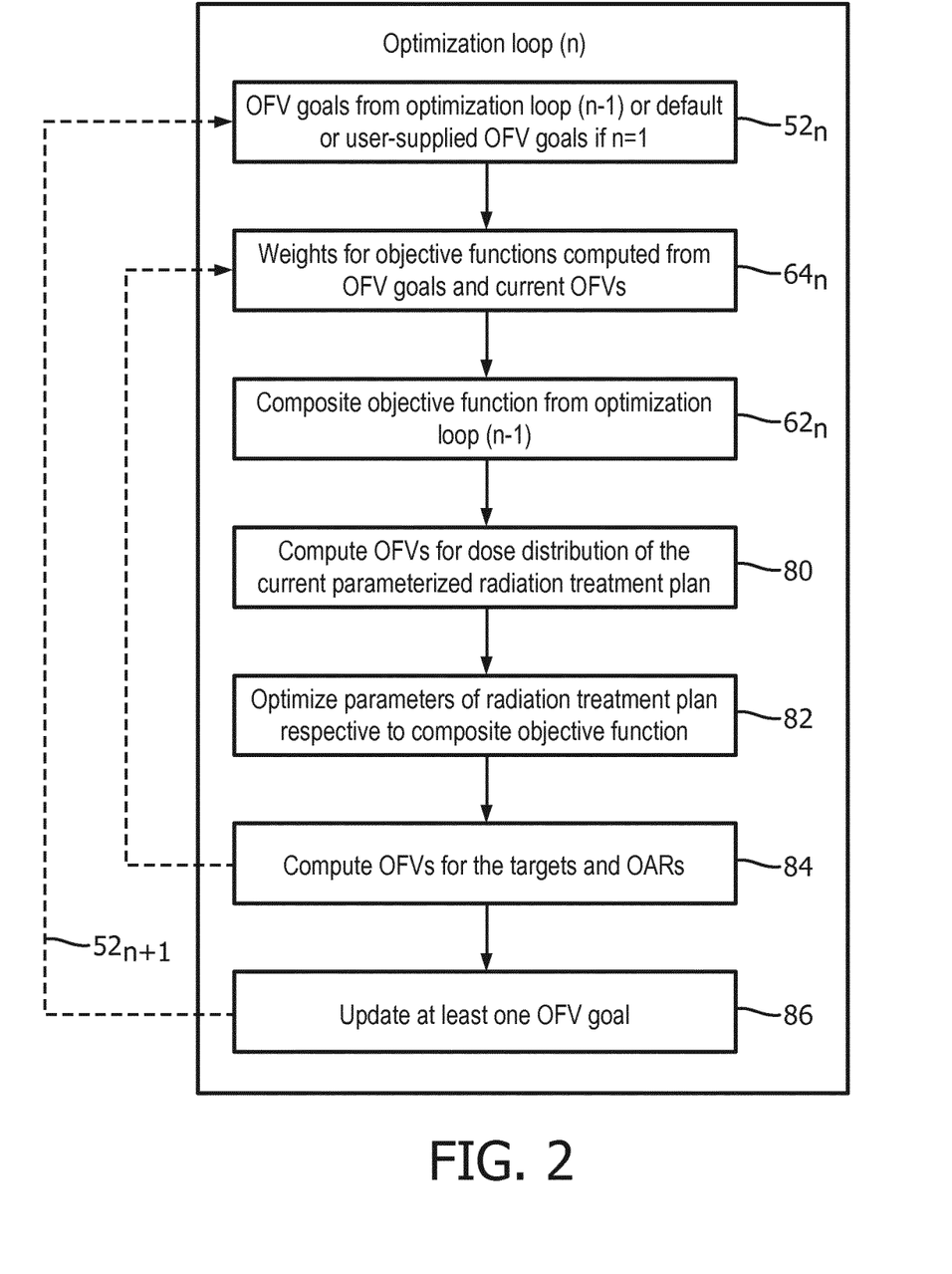
FIG. 2 diagrammatically shows one optimization loop (n) of a radiation treatment planning method suitably performed by the system of FIG. 1.

With continuing reference to FIG. 1 and with further reference to FIG. 2, an illustrative embodiment of one optimization loop, arbitrarily indexed as optimization loop n in FIG. 2, of the auto-planning process performed by the radiation therapy planning device 30 is described. Optimization loop n is initiated with OFV goals $52_n$ for the loop n. The OFV goals $52_n$ are output by the preceding optimization loop (n−1), unless n=1 (the initial optimization loop) in which case the OFV goals $52_{n=1}$ are suitably default values provided by a template and/or values supplied by the dosimetrist via the planning GUI 44. The weights $64_n$ and optionally dose levels for optimization loop n are computed from the OFV goals $52_n$ and the current OFVs. The composite objective function $62_n$ is then formulated as a weighted sum of the objective functions weighted by the weights $64_n$. In an operation 80, the OFVs are computed for the dose distribution 60 of the current parameterized radiation treatment plan output by the last iteration (n−1) (or, alternatively, the dose distribution is computed in operation 80 for the first time if n=1, using initial or default values for the plan parameters). In an operation 82, the radiation treatment plan optimizer 58 optimizes the parameters of the radiation treatment plan respective to the composite objective function $62_n$ of the current optimization loop n. In an operation 84, the objective function values for the OAR(s) and target(s) are updated, and in an operation 86 if the OFVs are out of the desired balance then at least one OFV goal is updated by the OFV goals updater 70 to produce updated OFV goals $52_{n+1}$ which serve as the OFV goals input to the next optimization loop (n+1). (Note, it is contemplated that some optimization loops might not include any OFV goal updates).

Figure 3:
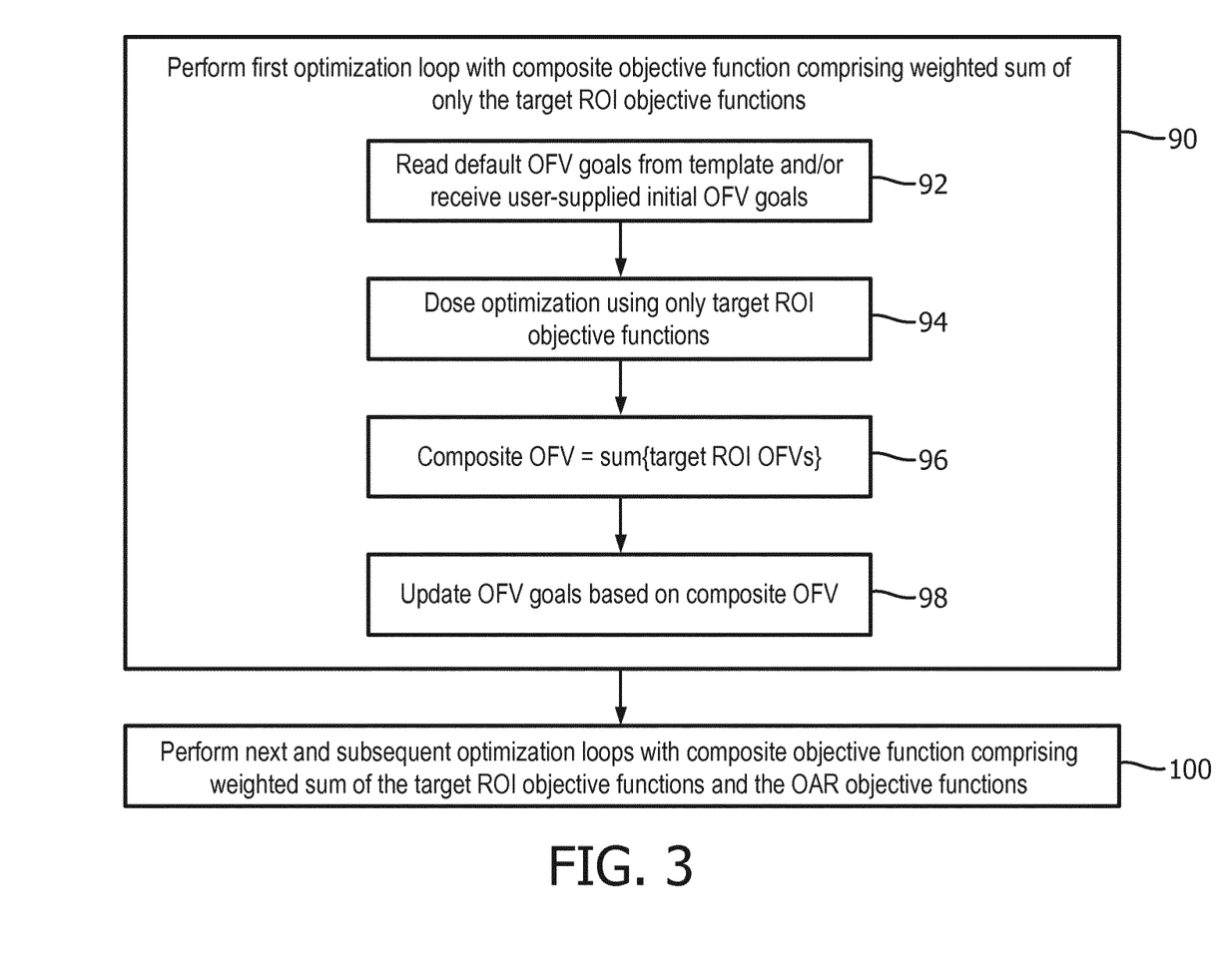
FIG. 3 diagrammatically shows a variant embodiment of the radiation treatment planning method in which the first optimization loop optimizes the dose distribution only with respect to the objective functions for the target region of interest.

With reference now to FIG. 3, in some embodiments the initial optimization loop (n=1) is handled differently from subsequent loops (n>1). Operation 90 diagrammatically depicted in FIG. 3 represents the first optimization loop (n=1). In an operation 92, default OFV goals are read from a template, and/or the user supplies OFV goals for the initial loop (n=1), e.g. by editing the default OFV goals presented in the table or spreadsheet via the planning GUI 44. In an operation 94, dose optimization is performed using only the target ROI objective functions. That is to say, for the first optimization loop 90 of the embodiment of FIG. 3, the composite objective function $62_{n=1}$ of FIG. 2 is a weighted sum of only those objective functions that quantify compliance of the computed dose distribution with corresponding objectives for a target ROI defined in the planning image 42. As a reminder, the ROIs defined in the planning image of the patient include at least one target ROI to be irradiated, such as a malignant tumor, and at least one organ-at-risk (OAR) ROI to be at least partly spared irradiation. In an operation 96, a composite OFV is computed as the sum of the OFVs of the target ROI objective functions. In an operation 98, the OFV goals are updated based on the composite OFV. Thereafter, in operation 96 the next and subsequent optimization loops (loop n=2, loop n=3, et cetera) are performed with the composite objective function comprising the weighted sum of the target ROI objective functions and the OAR objective functions as previously described with reference to FIG. 2. A rationale for the variant implementation 90 of the initial optimization loop n=1 is that by disregarding the OARs in the n=1 loop the resulting composite OFV represents the "best" composite objective function achievable for the target. This, then, provides a metric for the amount of "sparing" that can be allocated amongst the OARs.

In the following, a more detailed non-limiting example of the approach of FIG. 3 is presented. In the initial (n=1) optimization loop 90, the allowable composite target objective function is determined value based on dose optimization of only the target objective functions. This value is used to determine the extent to which subsequent optimization loops 100 can drive the OAR sparing harder or needs to back off. There are a number of implementations one could use to determine this value, such as a linear approach. However, in the illustrative example the following equation is employed:

$$\text{Composite objective functional value goal} = 2*(2*\text{targetToOAR})^{mult}*\text{baselineTargetOFV} \quad (1)$$

where targetToOAR is a balance factor, with the limiting case of targetToOAR=1 providing full OAR sparing and the limiting case of targetToOAR=0 maximizing priority to the target ROI. The term baselineTargetOFV is the objective function value result 96 after running the target only optimization 94. The exponential factor mult is a constant used to increase or limit the range of OAR sparing, and in some contemplated embodiments is hardcoded to the value of 8.

The OFV goal update operation 98 in this illustrative example is performed as follows. The OFV goal, denoted here as ofvGoal, for each objective function is determined in a dynamic mode by adapting ofvGoal to a ratio of the allowable target OFV and the current target OFV (allowableTargetOFV/targetCompValue). This ratio can be dampened to avoid over correction and then multiplied times the ofvGoal as follows:

$$\text{multiplier} = \text{allowableTargetOFV/targetCompValue}^{tuningDampening} \quad (2)$$

and $$\text{ofvGoal} = \text{ofvGoal}*\text{multiplier} \quad (3)$$

With the OFV goals determined according to Equations (2) and (3), the weights 64 (see FIG. 1) can be determined as follows. The new (i.e. adjusted) objective weight is denoted as adjWeight. The weight is ultimately what is tuned and effects the optimization. It is determined based on the ratio of ofvGoal and the current objective function value. Similarly to adjusting the threshold as per Equation (1), in the illustrative example there is a dampening parameter to avoid overcompensation of the weight:

$$\text{weight}*(\text{ofvGoal/OFV})^{weightDampening} \quad (4)$$

In one illustrative example, the weight is clipped between 100 and $10^{-8}$.

The disclosed approaches can be extended to improving other aspects of the radiation treatment plan between successive optimization loops.

For example, in another aspect, the target dose of an objective function that quantifies compliance of the computed dose distribution with a prescription dose is adjusted between optimization loops to obtain a desired coverage percentage and/or prescription percentage for a target or targets. Typically, the oncologist or radiologist specifies a prescription dose which is the radiation dose to be delivered to the target on a per unit volume (or mass) basis, e.g. in centigray (cGy) units of relative biological effectiveness (RBE). This is formulated as an objective function quantifying compliance of the computed dose distribution with the prescription dose for a target ROI (i.e. target), and the radiation treatment plan optimization attempts to obtain this prescription dose over the volume of the target, and may also include an objective enforcing uniformity over the target volume.

The oncologist or radiologist is also interested in ensuring that the volume of the target is well-covered, that is, that the entire target volume receives a dose that is equal to, or at least close to, the prescription dose. Commonly, after performing the optimization the cumulative dose volume histogram (cumulative DVH) for the volume is provided, which is a plot of the coverage percentage as a function of delivered dose (per unit volume), that is, the fraction of the target volume that receives at least the abscissa (i.e. x-coordinate) dose value. The cumulative DVH should ideally have unity value for lower dose values and exhibit a sharp cutoff at the point where the abscissa of the cumulative DVH reaches the prescription dose. On the other hand, a gradual roll-off below unity of the cumulative DVH as the abscissa approaches the prescription dose indicates that a substantial portion of the target volume is receiving less than the prescription dose according to the optimized radiation treatment plan. Those portions of the target that receive substantially less than the prescription dose are less likely to be necrotized by the radiation therapy, leading to lower therapeutic effectiveness as a substantial portion of the tumor (a typical target ROI) may survive the radiation therapy.

The coverage of a target is also sometimes expressed quantitatively by way of a prescription percentage value. This is the percentage of the prescription dose that the entire target volume receives. In other words, the prescription percentage is the dose value along the abscissa of the cumulative DVH at which the coverage fraction begins to decrease below unity. This formulation expresses the prescription percentage for the full volume, i.e. the percentage of the prescription dose that the entire target volume receives. More generally, the prescription percentage may be formulated for some lesser fraction of the volume, e.g. the prescription percentage is the percentage of the prescription dose that at least 95% (more generally, y %) of the target volume receives. This generalized formulation corresponds to the dose value along the abscissa of the cumulative DVH at which the coverage fraction decreases below y %. Note that if y %=100% then the prescription percentage for the full volume is obtained. Other quantitative metrics of the coverage of the target are also contemplated.

As previously mentioned, the optimization attempts to obtain the prescription dose over the volume of the target, and may also include an objective enforcing uniformity over the target volume. While the uniformity objective may provide some enforcement of higher coverage, it does not guarantee that a desired target coverage, e.g. expressed as a prescription percentage or as some other quantitative coverage metric, will be achieved by the optimized radiation treatment plan. The usual way to address this deficiency is to perform the plan optimization, and then oncologist or radiologist reviews the plotted cumulative DVH and (if provided) the prescription percentage. If the oncologist or radiologist determines from these data that the target coverage is too low, then a post-optimization rescaling of the prescription dose is attempted using the prescription parameters. In cases with multiple targets, only one target of (for example three) targets may have undesirable coverage, in which case it may be impossible to rescale the prescription dose. Furthermore, rescaling the prescription dose upward can result in higher radiation exposure to the organs at risk (OARs), possibly resulting in an OAR receiving an unacceptably high dose. Additionally, in some cases, rescaling can lead to an undeliverable radiation therapy plan.

Another possible approach would be to add a prescription percentage or min dose objective to the composite objective function. However, this approach tends not to be as effective or intuitive as multiple target objectives with different and sometimes conflicting goals are used.

In another approach disclosed herein, the target dose objective for a target volume is initialized at the prescription dose as usual; but, then is adjusted between optimization loops in a manner that drives the radiation treatment plan optimization toward improved matching with a desired target coverage, e.g. expressed as a prescription percentage for a fraction (y %) of the target volume or for the full target volume (y %=100%). In other words, the optimization loop includes determining a metric of coverage of the target ROI and adjusting the prescription dose based on comparison of the determined a metric of coverage of the target ROI and a desired coverage of the target ROI. This approach is based on the recognition that, while the prescription dose for a target (e.g. tumor) is of importance to the efficacy of the radiation therapy, achieving the desired prescription percentage is also of substantial or even greater importance, since an unacceptably low prescription percentage can lead to portions of the tumor being insufficiently irradiated to provide the desired necrotization.

Figure 4:
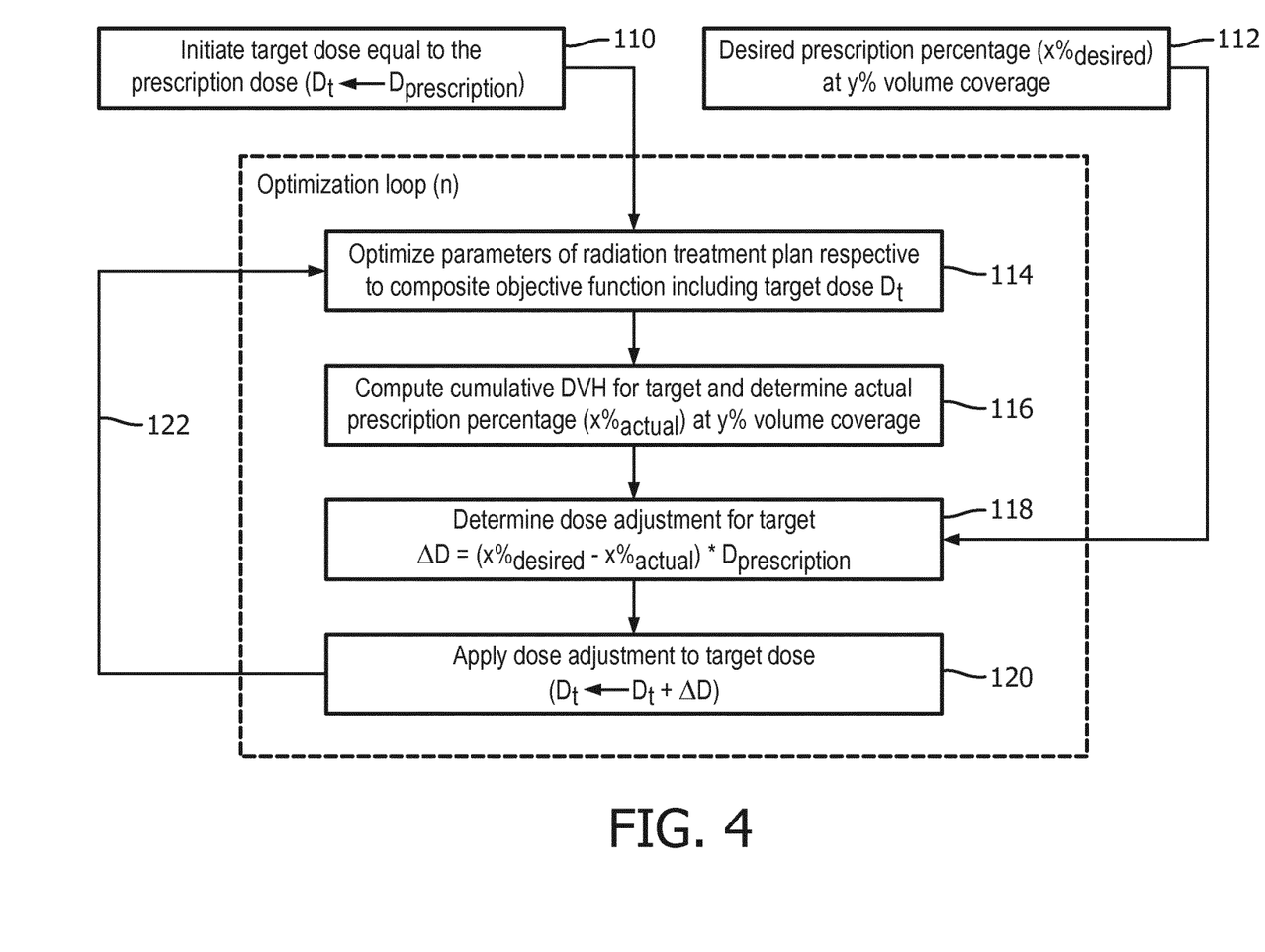
FIG. 4 diagrammatically shows an embodiment in which the prescription dose is adjusted between optimization loops to improve target coverage.

With reference now to FIG. 4, in an illustrative approach suitably performed by the electronic processor 32 of FIG. 1, the target dose ($D_t$) for a target volume (e.g. tumor) is initially set to the prescription dose ($D_{prescription}$) in an operation 110. The multi-loop optimization also receives a desired prescription percentage 112, e.g. expressed as the desired prescription percentage (X $\%_{desired}$) at y % volume coverage. As previously discussed, it is contemplated to employ the limiting case of y %=100% in which case the desired prescription percentage 112 is for full coverage of the target.

In an operation 114, the parameters of the radiation treatment plan are optimized respective to the composite objective function which includes a target dose objective corresponding to the target dose $D_t$, and which may also include an objective enforcing dose uniformity over the target volume. Of course, the composite objective function may include other objectives as discussed herein. The composite objective function does not include any objectives directly enforcing the desired prescription percentage 112.

In an operation 116, the cumulative DVH is computed for the target, and the actual prescription percentage (X $\%_{actual}$) at y % volume coverage is determined for the radiation treatment plan output by the optimization 114. In an operation 118, a dose adjustment ($\Delta D$) is computed according to:

$$\Delta D = (X\%_{desired} - X\%_{actual}) \times D_{prescription} \quad (5)$$

Thus, if the actual prescription percentage (X $\%_{actual}$) is lower than the desired prescription percentage (X $\%_{desired}$), then the dose adjustment is positive. If the actual prescription percentage is higher than that desired (i.e., X $\%_{actual}$>X $\%_{desired}$), then the dose adjustment may be a negative value obtained by applying Equation (5) or, in an alternative embodiment, if X $\%_{actual}$>X $\%_{desired}$ then in operation 118 the dose adjustment ($\Delta D$) is set to zero. The dose adjustment of Equation (5) is merely an illustrative example, and variant formulations are also contemplated. For example, a dampening factor could be incorporated, in which a dampening factor value less than 1 would reduce the correction and a value greater than 1 would increase the correction.

In an operation 120 the dose adjustment $\Delta D$ from operation 118 is applied to adjust the target dose $D_t$ according to:

$$D_t \leftarrow D_t + \Delta D \quad (6)$$

Although not shown in FIG. 4, it will be appreciated that the optimization loop may further include various adjustments of objective function value (OFV) goals, e.g. as described previously herein with reference to FIG. 2. As diagrammatically indicated in FIG. 4 by flow arrow 122, after these adjustments the process flow returns to operation 114 to perform the radiation treatment plan optimization of the next optimization loop.

Figure 5:
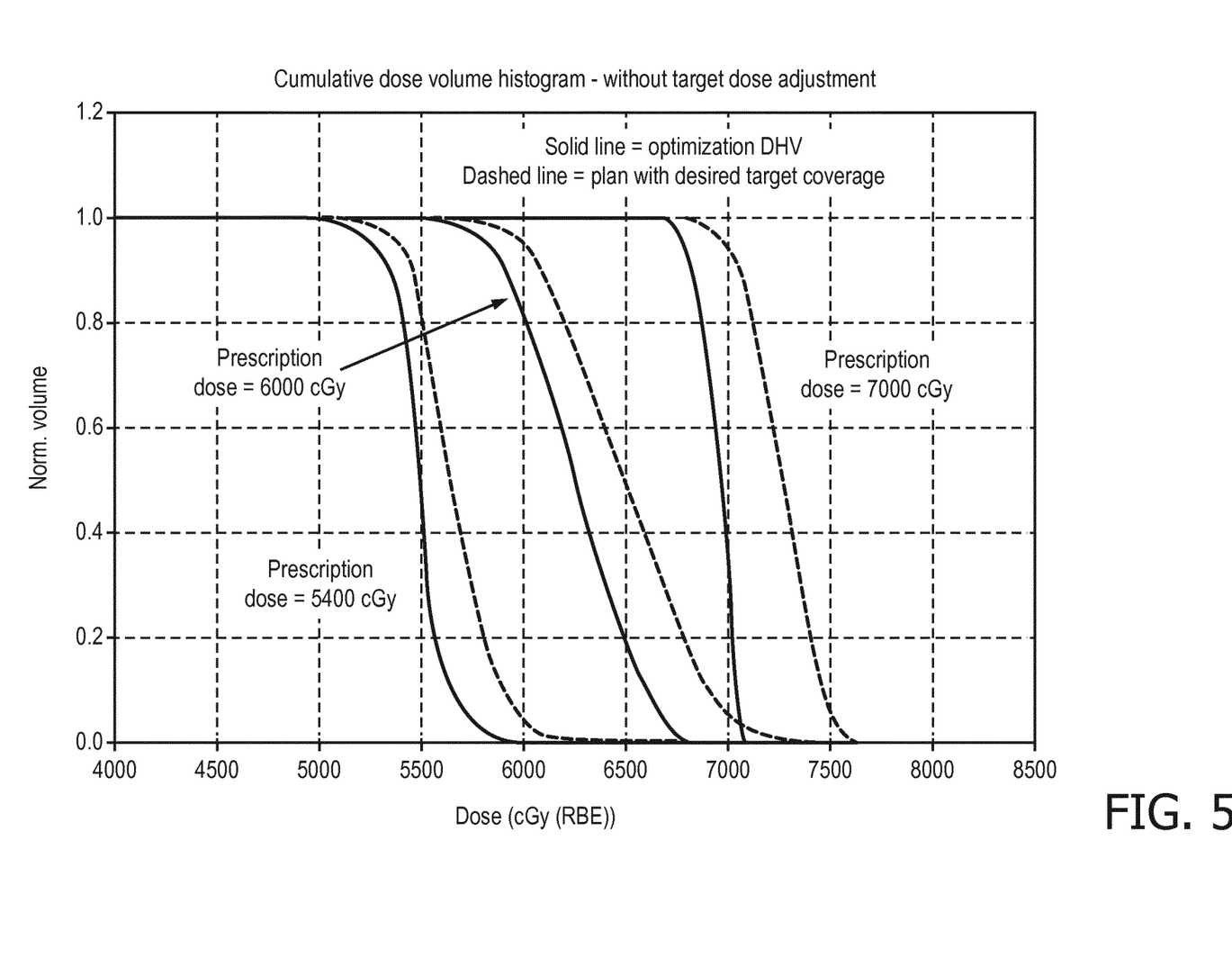
FIGS. 5 and 6 show Cumulative Dose Volume Histogram (DVH) plots for optimized radiation treatment plans (solid lines) and for a plan with desired target coverage (dashed lines), at indicated prescription doses of 5400 cGy, 6000 cGy, and 7000 cGy, where the optimization is without target dose adjustment between optimization loops (FIG. 5) and with target dose adjustment between optimization loops (FIG. 6).
Figure 6:
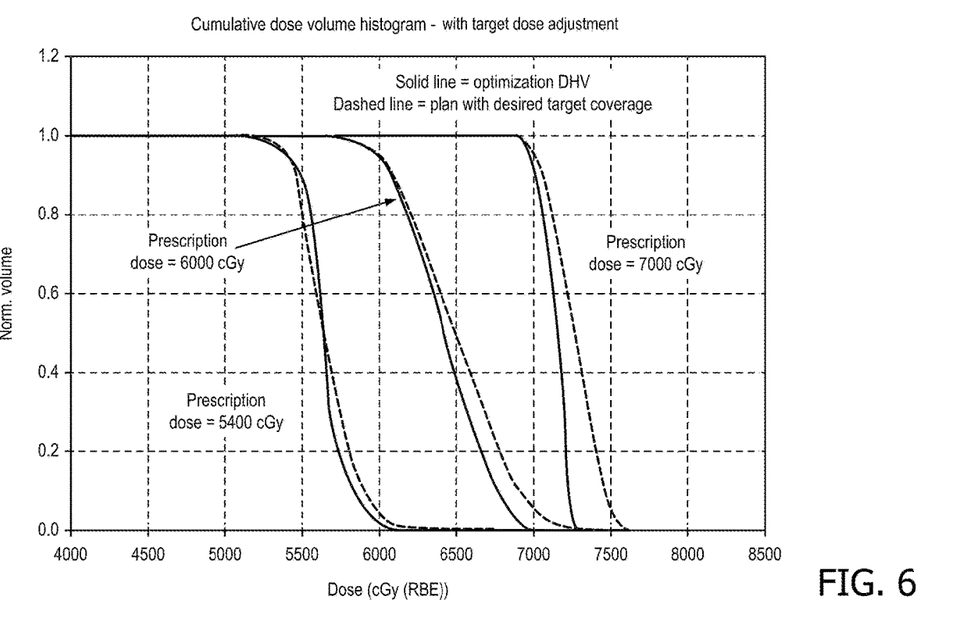

FIGS. 5 and 6 show Cumulative Dose Volume Histogram (DVH) plots for optimized radiation treatment plans (solid lines) and for a plan with desired target coverage (dashed lines), at indicated prescription doses ($D_{prescription}$) of 5400 cGy, 6000 cGy, and 7000 cGy, where the optimization is without target dose adjustment between optimization loops (FIG. 5) and with target dose adjustment between optimization loops (FIG. 6). As can be seen by comparing FIGS. 5 and 6, the target dose adjustments (FIG. 6) result in improved matching with the desired target coverage.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A non-transitory storage medium storing instructions, readable and executable by a computer, for determining a radiation treatment plan for delivering radiation treatment to a patient using a radiation delivery device, wherein when executed, the instructions cause the computer to:
   perform a plurality of optimization loops wherein each optimization loop includes:
   computing a dose distribution in the patient represented by a planning image of the patient with regions of interest (ROIs) defined in the planning image wherein the dose distribution is to be delivered by the radiation delivery device represented by a radiation delivery device model executing a parameterized radiation treatment plan;
   determining weights for objective functions, wherein each objective function corresponds to an objective, has an objective function value (OFV), and quantifies compliance of the computed dose distribution with the corresponding objective for a ROI defined in the planning image, and wherein the weights are determined from OFV goals for the OFVs of the objective functions; and
   producing an optimized dose distribution by adjusting parameters of the parameterized radiation treatment plan to optimize the computed dose distribution in the patient respective to a composite objective function comprising a weighted sum of the objective functions weighted by the determined weights for the objective functions,
   wherein at least one optimization loop of the plurality of optimization loops further includes automatically updating at least one OFV goal, wherein the updated at least one OFV goal is used in at least a next-performed optimization loop;
   store an optimized radiation treatment plan comprising the parameterized radiation treatment plan with the adjusted parameters corresponding to the optimized dose distribution produced by a last-performed optimization loop of the plurality of optimization loops; and,
   deliver the optimized radiation treatment plan to the radiation delivery device for executing the optimized radiation treatment plan delivering the radiation treatment to the patient.

2. The non-transitory storage medium of claim 1 wherein the automatic updating of the at least one OFV goal includes scaling the OFV goal by a multiplier that is functionally dependent on the OFV of the corresponding objective function for the optimized dose distribution produced by the optimization loop.

3. The non-transitory storage medium of claim 1 wherein the ROIs defined in the planning image of the patient include at least one target ROI to be irradiated and at least one organ-at-risk (OAR) ROI to be at least partly spared irradiation, and wherein:
   for a first-performed optimization loop of the plurality of optimization loops, the composite objective function comprises a weighted sum of only objective functions that quantify compliance with a corresponding objective for a target ROI;
   for optimization loops of the plurality of optimization loops performed after the first-performed optimization loop, the composite objective function comprises a weighted sum of the objective functions that quantify compliance with a corresponding objective for a target ROI and the objective functions that quantify compliance with a corresponding objective for an OAR ROI; and
   the first-performed optimization loop further includes automatically updating the OFV goals based on a value of the composite objective function for the optimized dose distribution produced by the first-performed optimization loop, the updated OFV goals being used in at least a second-performed optimization loop of the plurality of optimization loops.

4. The non-transitory storage medium of claim 1 wherein determining the weights for the objective functions in each optimization loop comprises scaling a current weight for each objective function by a scaling factor functionally dependent on a ratio of the OFV goal for the objective function and the OFV of the objective function for the computed dose distribution prior to the optimization loop adjusting the parameters of the parameterized radiation treatment plan.

5. The non-transitory storage medium of claim 1 wherein at least one objective function quantifies compliance of the computed dose distribution with a prescription dose for a target ROI and at least one optimization loop of the plurality of optimization loops further includes determining a metric of coverage of the target ROI and adjusting the objective function quantifying compliance with the prescription dose for the target ROI based on a comparison of the determined a metric of coverage of the target ROI and a desired coverage of the target ROI; wherein the metric of coverage of the target ROI is a prescription percentage at a specified volume coverage of the target ROI and the adjusting includes increasing a target dose of the objective function quantifying compliance with the prescription dose for the target ROI if the prescription percentage at the specified volume coverage of the target ROI is less than a desired prescription percentage at the specified volume coverage of the target ROI .

6. The non-transitory storage medium of claim 1 wherein at least one optimization loop of the plurality of optimization loops further includes reformulating or adjusting at least one objective function based on the OFV goal for the objective function and the OFV of the objective function for the optimized dose distribution produced by the optimization loop.

7. The non-transitory storage medium of claim 6 wherein the objective functions include at least two of:
   a minimum dose (Min Dose) objective function that quantifies compliance with a minimum dose objective for a ROI;
   a maximum dose (Max Dose) objective function that quantifies compliance with a maximum dose objective for a ROI;
   a minimum dose to a given volume (Min dose volume histogram (DVH)) objective function that quantifies compliance with a minimum dose objective for a given fraction of a volume of an ROI; and
   a maximum dose to a given volume (Max DVH) objective function that quantifies compliance with a maximum dose objective for a given fraction of the volume of an ROI.

8. The non-transitory storage medium of claim 7 wherein the parameters of the parameterized radiation treatment plan include at least one of:
multi-leaf collimator settings;
beamlet weights; or
one or more beam arc parameters.

9. A method of delivering radiation treatment to a patient using a radiation delivery device, the method comprising:
formulating objective functions corresponding to objectives of a radiation treatment plan, each objective function having an objective function value (OFV), wherein each objective function quantifies dose distribution compliance with the corresponding objective for a region of interest defined in a planning image of the patient;
performing a plurality of optimization loops wherein each optimization loop includes:
determining weights for the objective functions from at least objective function value (OFV) goals for the OFVs of the objective functions;
computing a dose distribution in the patient represented by the planning image wherein the dose distribution is to be delivered by the radiation delivery device represented by a radiation delivery device model executing a parameterized radiation treatment plan; and
producing an optimized radiation treatment plan with an optimized dose distribution by adjusting parameters of the parameterized radiation treatment plan to optimize the computed dose distribution in the patient respective to a composite objective function comprising a weighted sum of the objective functions weighted by the determined weights,
wherein at least one optimization loop further includes updating the OFV goal of at least one objective function,, wherein the updated OFV goal is used in at least the next-performed optimization loop; and
operating the radiation delivery device to execute the optimized radiation treatment plan when delivering the radiation treatment to the patient.

10. The method of claim 9 wherein the updating of the OFV goal of at least one objective function comprises automatically updating the OFV goal based on the OFVs of the objective functions for the optimized dose distribution produced by the optimization loop.

11. The method of claim 9 wherein the updating of the OFV goal of at least one objective function comprises scaling the OFV goal by a scaling factor functionally dependent on a ratio of the OFV goal and the OFV of the objective function for the optimized dose distribution produced by the optimization loop.

12. The method of claim 9 wherein the ROIs defined in the planning image of the patient include at least one target ROI to be irradiated and at least one organ-at-risk (OAR) ROI to be at least partly spared irradiation, and wherein:
for a first-performed optimization loop the composite objective function comprises a weighted sum of only the objective functions that quantify compliance with a corresponding objective for a target ROI;
for the optimization loops performed after the first-performed optimization loop, the composite objective function comprises a weighted sum of the objective functions that quantify compliance with a corresponding objective for a target ROI and the objective functions that quantify compliance with a corresponding objective for an OAR ROI; and the first-performed optimization loop further includes automatically updating the OFV goals of the objective functions based on a value of the composite objective function for the optimized dose distribution produced by the first-performed optimization loop, the updated OFV goals of the objective functions being used in at least a second-performed optimization loop.

13. The method of claim 9 wherein at least one objective function quantifies compliance of the computed dose distribution with a prescription dose for a target ROI and at least one optimization loop further includes determining a prescription percentage at a specified volume coverage of the target ROI and adjusting the objective function quantifying compliance with the prescription dose for the target ROI based on a comparison of the determined prescription percentage and a desired prescription percentage at the specified volume coverage of the target ROI; wherein:
the objective function that quantifies compliance of the computed dose distribution with the prescription dose for the target ROI penalizes deviation from a target dose in the target ROI wherein the target dose is initially set equal to the prescription dose; and
the adjusting increases the target dose if the determined prescription percentage is lower than a desired prescription percentage at the specified volume coverage of the target ROI.

14. The method of claim 9 wherein determining the weights for the objective functions in each optimization loop comprises scaling a current weight for each objective function by a scaling factor functionally dependent on a ratio of the OFV goal for the objective function and the OFV of the objective function for the computed dose distribution prior to the optimization loop adjusting the parameters of the parameterized radiation treatment plan.

15. A radiation therapy planning and delivery system, comprising:
a radiation delivery device for delivering radiation treatment to a patient in accordance with an optimized radiation treatment plan;
an electronic processor; and
a non-transitory storage medium storing instructions readable and executable by the electronic processor to determine the optimized radiation treatment plan by performing a plurality of optimization loops wherein each optimization loop includes:
computing a dose distribution in the patient represented by a planning image, wherein the dose distribution is to be delivered by the radiation delivery device represented by a radiation delivery device model executing a parameterized radiation treatment plan;
determining weights for objective functions, wherein each objective function corresponds to an objective, has an objective function value (OFV), and quantifies compliance of the computed dose distribution with the corresponding objective for a target region of interest (ROI) defined in the planning image, and wherein the weights are determined from OFV goals for the OFVs of the objective functions; and
producing an optimized dose distribution by adjusting parameters of the parameterized radiation treatment plan to obtain the optimized radiation treatment plan to optimize the computed dose distribution in the patient respective to a composite objective function comprising a weighted sum of objective functions including an objective function quantifying compliance with a target dose for the target ROI wherein the target dose is initially set to a prescription dose;

wherein at least one optimization loop of the plurality of optimization loops further includes updating the target dose based on a comparison of a metric of coverage of the target ROI and a desired coverage of the target ROI, wherein the updated target dose is used in at least the next-performed optimization loop; and wherein at least one other optimization loop of the plurality of optimization loops further includes updating at least one OFV goal, wherein the updated at least one OFV goal is used in at least a next-performed optimization loop.

16. The system of claim 15 wherein the metric of coverage is a prescription percentage at a specified volume coverage of the target ROI.

17. The system of claim 16 wherein the updating comprises increasing the target dose if the prescription percentage determined for the optimized dose distribution is less than a desired prescription percentage at the specified volume coverage of the target ROI.

18. The system of claim 16 wherein the updating comprises:

adjusting the target dose by an amount proportional to (X $\%_{desired}$–X $\%_{actual}$) where X $\%_{actual}$ is the prescription percentage determined for the optimized dose distribution and X $\%_{desired}$ is a desired prescription percentage at the specified volume coverage of the target ROI.

19. The non-transitory storage medium of claim 1, wherein the OFV goals are fixed template values for a type of the radiation treatment being determined.

* * * * *